(12) United States Patent
Felding et al.

(10) Patent No.: US 8,350,026 B2
(45) Date of Patent: Jan. 8, 2013

(54) VEGF-2 RECEPTOR AND PROTEIN TYROSINE KINASE INHIBITORS AND PHARMACEUTICAL USE THEREOF

(75) Inventors: Jakob Felding, Charlottenlund (DK); Xifu Liang, Glostrup (DK); Anne Marie Horneman, Humlebaek (DK); Tina Dahlerup Poulsen, Brønshøj (DK); Jens Christian Højland Larsen, Kgs. Lyngby (DK)

(73) Assignee: Leo Pharma A/S, Ballerup (DK)

( * ) Notice: Subject to any disclaimer, the term of this patent is extended or adjusted under 35 U.S.C. 154(b) by 0 days.

(21) Appl. No.: 13/058,797

(22) PCT Filed: Aug. 27, 2009

(86) PCT No.: PCT/DK2009/000190
§ 371 (c)(1),
(2), (4) Date: Apr. 19, 2011

(87) PCT Pub. No.: WO2010/022725
PCT Pub. Date: Mar. 4, 2010

(65) Prior Publication Data
US 2011/0190282 A1    Aug. 4, 2011

Related U.S. Application Data

(60) Provisional application No. 61/092,213, filed on Aug. 27, 2008.

(30) Foreign Application Priority Data
Oct. 17, 2008  (DK) .................. 2008 01449

(51) Int. Cl.
C07D 213/72   (2006.01)
C07D 405/12   (2006.01)
C07D 413/06   (2006.01)
C07D 413/12   (2006.01)

(52) U.S. Cl. .............. 544/96; 546/271.4; 546/283.4; 546/309

(58) Field of Classification Search .......... None
See application file for complete search history.

(56) References Cited

U.S. PATENT DOCUMENTS

| 7,148,357 B2* | 12/2006 | Huth et al. ............. 546/275.7 |
| 2003/0176469 A1 | 9/2003 | Seidelmann et al. |
| 2006/0116380 A1* | 6/2006 | Bohlmann et al. ....... 514/252.04 |
| 2006/0160861 A1* | 7/2006 | Bohlmann et al. ............ 514/338 |
| 2006/0264425 A1* | 11/2006 | Bohlmann et al. ......... 514/227.5 |

FOREIGN PATENT DOCUMENTS

| WO | WO 01/55114 A1 | 8/2001 |
| WO | WO 01/85691 A1 | 11/2001 |
| WO | WO 2005/054179 A2 | 6/2005 |

OTHER PUBLICATIONS

Vippagunta et al., Crystalline solids, 48 Adv. Drug Delivery Rev. 3-26 (2001).*
International Search Report for PCT/DK2009/000190, mailed Nov. 2, 2009.

* cited by examiner

*Primary Examiner* — Janet Andres
*Assistant Examiner* — Timothy R. Rozof
(74) *Attorney, Agent, or Firm* — Birch, Stewart, Kolasch & Birch, LLP

(57) ABSTRACT

The invention relates to compounds of general formula (I) wherein W, D, E, G, J, L, $R_1$, $R_2$, $R_3$, $R_4$, $R_5$ and Y are as defined herein, and pharmaceutically acceptable salts, hydrates, or solvates thereof, for use—alone or in combination with one or more other pharmaceutically active compounds—in therapy, for treating diseases associated with deregulated angiogenesis, such as cancer and skin and eye diseases.

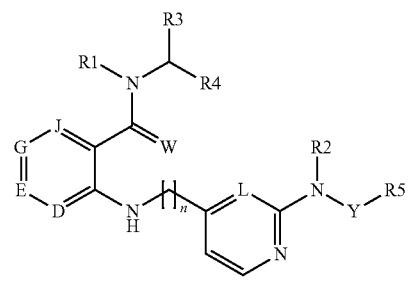

(I)

11 Claims, No Drawings

VEGF-2 RECEPTOR AND PROTEIN TYROSINE KINASE INHIBITORS AND PHARMACEUTICAL USE THEREOF

CROSS REFERENCE TO RELATED APPLICATIONS

This National Phase application claims benefit of PCT/DK2009/000190 filed on Aug. 27, 2009, which claims benefit under 35 U.S.C §119(e) of U.S. Provisional Application No. 61/092,213 filed on Aug. 27, 2008, and under 35 U.S.C §119 (a) to Patent Application No. PA 2008 01449 filed in Denmark, on Oct. 17, 2008. The entire contents of all of the above applications are hereby incorporated by reference into the present application.

FIELD OF THE INVENTION

This invention relates to novel VEGFR-2 receptor and protein tyrosine kinase inhibitors, to said compounds for use in therapy, to pharmaceutical compositions comprising said compounds, to methods of treating diseases comprising administering to a patient in need thereof an effective amount of said compound, and to the use of said compounds in the manufacture of medicaments.

BACKGROUND OF THE INVENTION

This invention relates to novel compounds which can inhibit angiogenesis, i.e. which can inhibit the generation or maturation of new blood vessels. It is believed that said compounds may be beneficial in the treatment of a variety of diseases, such as atherosclerosis, inflammatory conditions such as dermatitis, psoriasis, rosacea and rheumatoid arthritis, eye diseases such as diabetic retinopathy and macular degeneration as well as cancer.

It is now widely accepted that blocking angiogenesis around tumours could be a viable way of treating cancer, possibly as an adjuvant treatment. This is also reflected in the large number of development projects and clinical trials with angiogenesis inhibitors with different inhibitory approaches. There are 5 launched drugs and more than 30 agents in development that aim to restrict angiogenesis by inhibiting VEGF/VEGFR signalling.

This way of blocking angiogenesis is of particular interest for the present invention, which relates to VEGF receptor inhibitors, most particularly VEGFR-2 (KDR) receptor inhibitors. Sorafenib and Sunitinib were both launched in 2006 and both target, amongst others, VEGFR-2. Sunitinib inhibits VEGFR-2 and PDGFR-β with $IC_{50}$ values of 9 and 8 nM respectively. Whilst the developers of Sorafenib have concentrated on improving its activity against Raf-1 kinase, it also exhibits an $IC_{50}$ of 22 nM for VEGFR-2. Kiselyov et al. have reviewed such inhibitors in clinical trials in *Expert Opin. Investig. Drugs* (2007) 16(1):83-107.

A number of studies have been carried out investigating the role of VEGF and its receptors VEGF-R1 and VEGF-R2 in skin diseases such as rosacea. Rosacea is a common chronic condition affecting mainly the facial skin and characterised by visible blood vessels, central facial erythema and often papules and pustules. The pathogenesis of the disease has not been fully explained, but a link, especially in the case of non-phymatous rosacea, with VEGF has been suggested by Smith J R et al. [Br J Opthalmol 2007; 91:226-229] and Gomaa A H A et al. [J Cutan Pathol 2007; 34:748-753]

There is also clear evidence to suggest that increased expression of angiogenic factors, in particular VEGF, is a central cause of proliferative diabetic retinopathy (PDR). In this condition, and others such as retinopathy of prematurity, sickle cell retinopathy, age-related macular degeneration, retina vein occlusion and Eales disease, preretinal vascularisation is a major cause of blindness. New blood vessels grow from the inner retinal vasculature into the vitreous humour. This can cause visual loss by vitreous haemorrhage and/or tractional retinal detachment due to contraction of the fibrous tissue associated with the new blood vessels. Recently, pharmaceutical companies have been investigating drug targets to inhibit the angiogenic pathways, with TG100801, which inhibits both VEGFR-2 and Src kinases currently in clinical trials for the treatment of age-related macular degeration. Other inhibitors of the VEGF pathway intended to treat eye disease are discussed by Slevin et al. in *Expert Opin. Investig. Drugs* (2008) 17(9):1301-1314.

WO 01/29009 and WO 01/58899 describe pyridine derivatives as inhibitors of the VEGF receptor tyrosine kinase and the VEGF-dependent cell proliferation.

WO 02/090346 describes phthalazine derivatives as inhibitors of the VEGF receptor tyrosine kinase with angiogenesis inhibiting activity.

WO 04/056806 teaches 2-(1-H-indazol-6-ylamino)-benzamide compounds as protein kinases inhibitors which may be useful for the treatment of ophthalmic diseases.

PCT publications WO 00/27819, WO 00/27820, WO 01/55114, WO 01/81311, WO 01/85671, WO 01/85691, WO 01/85715, WO 02/055501, WO 02/066470, WO 02/090349, WO 02/090352, WO 03/000678, WO 02/068406, WO 03/040101, and WO 03/040102 all teach anthranilic acid amide derivatives which include compounds of general structure A, their preparation and their use as VEGF receptor tyrosine kinase inhibitors for the treatment of diseases associated with VEGF-dependent cell proliferation.

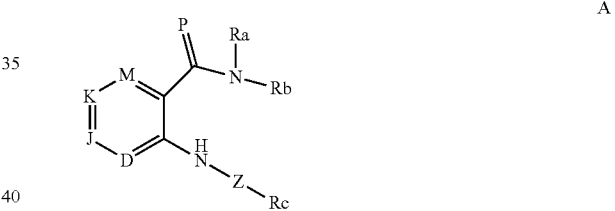

A

The use of anthranilic acid amide derivatives for other therapeutic purposes have previously been disclosed in, e.g. U.S. Pat. No. 3,409,688 (analgesic, anti-inflammatory, anti-ulcer), and in EP 564,356 (angiotensin II antagonist).

PCT publications WO 02/06213 and WO 99/01426 teach substituted phenylamino benzhydroxamic acid derivatives which include compounds of general structure B as MEK inhibitors, pharmaceutical compositions and methods of use thereof.

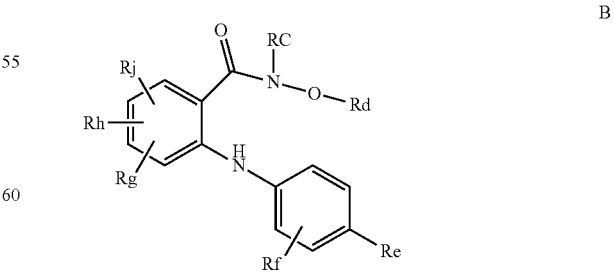

B

U.S. Pat. No. 5,155,110 teaches hydroxamic acid derivatives having cyclooxygenase and 5-lipoxygenase inhibiting properties and pharmaceutical compositions for treating conditions advantageously affected by the inhibition. The reference fails to describe tyrosine kinase inhibitory activity of the hydroxamic acid ester derivatives disclosed.

WO 05/054179 describes hydroxamic acid ester derivatives having the general structure C as angiogenesis inhibitors that act by inhibiting VEGF receptors, in particular VEGFR-2 (KDR) receptors.

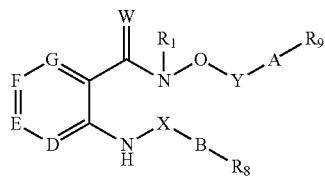

[C]

It is further envisaged that compounds of the present invention may be useful as inhibitors of other kinases such as protein tyrosine kinases of the Src family such as Src, Yes, Fyn, Lyn, Fgr, Lck and/or Hck, and/or JAK-2, and/or Raf-1, and/or cKit, and/or Fma/CSF-1R protein tyrosine kinases and as such show utility in the treatment of inflammatory and non-infectious autoimmune diseases wherein these kinases are involved.

Protein tyrosine kinases are a family of enzymes catalysing the transfer of the terminal phosphate of adenosine triphosphate to tyrosine residues in protein substrates. Phosphorylation of tyrosine residues on protein substrates leads to transduction of intracellular signals which regulate a wide variety of intracellular processes such as growth and activation of cells of the immune system, e.g. T-cells. As T-cell activation is implicated in a number of inflammatory conditions and other disorders of the immune system (e.g. autoimmune diseases), modulation of the activity of protein tyrosine kinases appears to be an attractive route to the management of inflammatory diseases. A large number of protein tyrosine kinases have been identified which may be receptor protein tyrosine kinases, e.g. the insulin receptor, or non-receptor protein tyrosine kinases.

Protein tyrosine kinases of the Src family have been found to be particularly important for intracellular signal transduction related to inflammatory responses (cf. D. Okutani et al., Am. J. Physiol. Lung Cell Mol. Physiol. 291, 2006, pp. L129-L141; C. A. Lowell, Mol. Immunol. 41, 2004, pp. 631-643). While some of Src family protein tyrosine kinases, e.g. Src, Yes and Fyn, are expressed in a variety of cell types and tissues, the expression of others is restricted to specific cell types, e.g. hematopoietic cells. Thus, the protein tyrosine kinase Lck is expressed almost exclusively in T-cells as the first signalling molecule to be activated downstream of the T-cell receptor, and its activity is essential for T-cell signal transduction. Expression of Hck, Lyn and Fgr is increased by inflammatory stimuli such as LPS in mature monocytes and macrophages. Also, if gene expression of the main B-cell Src family kinases, namely Lyn, Fyn and Blk, is disrupted, immature B-cells are prevented from developing into mature B-cells. Src family kinases have also been identified as essential for the recruitment and activation of monocytes, macrophages and neutrophils as well as being involved in the inflammatory response of tissue cells. For example, it has been found that expression of Hck, Lyn and Fgr is increased by inflammatory stimuli such as LPS in mature monocytes and macrophages.

A substantial number of autoimmune and inflammatory diseases involve the activation of T-cells and B-cells as well as other cells of the immune system such as monocytes and macrophages. Compounds which are capable of inhibiting activation of these cell types are therefore regarded as useful therapeutic agents in the treatment of such diseases.

SUMMARY OF THE INVENTION

The present inventors have surprisingly found that a novel class of amides and thioamides exhibit a high receptor tyrosine kinase inhibitory activity on a particular VEGF receptor, namely VEGFR-2, frequently referred to as the KDR receptor.

It is also envisaged that the novel anthranilic acid amides of the present invention may exhibit a high protein tyrosine kinase inhibitory activity on Src family, and/or JAK-2, and/or Raf-1, and/or cKit, and/or Fma/CSF-1R protein tyrosine kinases.

The novel anthranilic acid amides of the present invention may have a number of advantages in comparison to known structurally related anthranilic acid amides and in relation to the hydroxamic acid ester derivatives of WO 05/054179.

Compounds of the present invention may have improved pharmacokinetic properties such as improved solubility and absorption, reduced adverse side effects and decreased metabolic stability in comparison to known structurally related anthranilic acid amides. A particular advantage of the compounds of the present invention compared with the compounds of WO 05/054179 is that they are more easily metabolised.

In addition, in relation to the hydroxamic ester derivatives of WO 05/054179, the compounds of the present invention exhibit improved light stability in addition to increased or similar receptor affinity. Light stability is a desirable property for any compound intended for pharmaceutical use, but is especially important for compounds intended to treat, amongst other conditions, skin complaints such as psoriasis, dermatitis and rosacea or ophthalmic complaints associated with deregulated angiogenesis.

Accordingly, the invention relates to compounds of general formula I

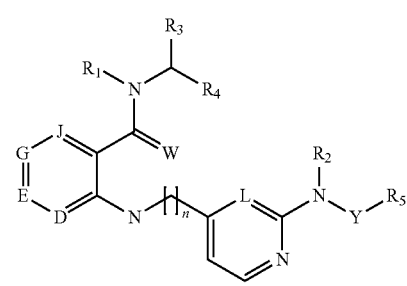

[I]

wherein $R_1$, $R_2$ and $R_3$ represent hydrogen or a straight or branched saturated or unsaturated $C_{1-6}$ hydrocarbon radical;
D represents nitrogen or CH;
E represents nitrogen or CH;
G represents nitrogen or CH;
J represents nitrogen or CH;
L represents nitrogen or CH;
n represents an integer from 1-2;
W represents oxygen or sulphur;
$R_4$ represents hydrogen, $C_{1-10}$alkyl, $C_{2-10}$alkenyl, $C_{2-40}$alkynyl, $C_{1-6}$hydroxyalkyl, $C_{3-8}$cycloalkyl, $C_{3-8}$cycloalkenyl, $C_{2-7}$heterocycloalkyl, $C_{6-12}$aryl, $C_{3-12}$heteroaryl or $C_{2-7}$heterocycloalkenyl wherein said $C_{1-10}$alkyl, $C_{2-10}$alkenyl, $C_{2-10}$alkynyl, $C_{1-6}$hydroxyalkyl, $C_{3-8}$cycloalkyl, $C_{3-8}$cycloalkenyl, $C_{2-7}$heterocycloalkyl, $C_{6-12}$aryl, $C_{3-12}$heteroaryl or $C_{2-7}$heterocycloalkenyl are optionally substituted by one or more, same or different substituents independently selected from the group consisting of hydrogen, halogen, oxo, hydroxy, trifluoromethyl, carboxy, cyano, $C_{2-6}$alkenyl, $C_{1-6}$alkoxy, $C_{1-6}$alkoxycarbonyl, $C_{1-6}$alkylthio, trifluoromethyl, $C_{3-8}$cycloalkyl, $C_{3-8}$cycloalkenyl, $C_{2-7}$heterocycloalkyl, $C_{2-7}$heterocycloalkenyl, $C_{6-12}$aryl, $C_{3-12}$heteroaryl and $C_{1-3}$alkylamino wherein said $C_{1-6}$alkyl, $C_{2-6}$alkenyl, $C_{1-6}$alkoxy, $C_{1-6}$alkoxycarbonyl, $C_{1-6}$alkylthio, trifluoromethyl, $C_{3-8}$cycloalkyl, $C_{3-8}$cycloalkenyl, $C_{2-7}$heterocycloalkyl, $C_{2-7}$heterocycloalkenyl, $C_{6-12}$aryl, $C_{3-12}$heteroaryl and $C_{1-3}$alkylamino are optionally substituted by one or more, same or different substituents independently selected from hydroxy, $C_{1-4}$alkyl, $C_{1-4}$alkyloxycarbonyl;

or $R_3$ and $R_4$ together forms part of a $C_{3-8}$cycloalkyl;

Y represents carbonyl or thioxo;

$R_5$ represents hydrogen, $C_{1-6}$alkyl, $C_{1-6}$alkylamino, $C_{1-6}$alkoxy, $C_{3-8}$cycloalkyl, $C_{3-8}$cycloalkenyl, $C_{2-7}$heterocycloalkyl or $C_{2-7}$heteroaryl, wherein said $C_{1-6}$alkyl, $C_{1-6}$alkylamino, $C_{1-6}$alkoxy, $C_{3-8}$cycloalkyl, $C_{2-7}$heterocycloalkyl or $C_{2-7}$heteroaryl are optionally substituted with one or more substituents independently selected from the group consisting of cyano, $C_{1-6}$alkyl, $C_{1-6}$alkoxycarbonyl or $C_{1-6}$alkylcarbonyloxy;

and pharmaceutically acceptable salts, hydrates, or solvates thereof.

In another aspect, the invention relates to pharmaceutical compositions comprising a compound of formula I or a pharmaceutically acceptable salt, hydrate, or solvate thereof together with a pharmaceutically acceptable vehicle or excipient.

In a further aspect, the invention relates to method of preventing, treating or ameliorating diseases or conditions associated with abnormal angiogenesis, the method comprising administering an effective amount of a compound according to formula I to a patient in need thereof.

In still a further aspect, the invention relates to compounds according to formula I for use in therapy.

In still a further aspect, the invention relates to compounds according to formula I for use in the treatment or amelioration of eye or skin diseases associated with deregulated angiogenesis.

In still a further aspect, the invention relates to the use of compounds according to formula I for the manufacture of a medicament for the prophylaxis, treatment or amelioration of eye diseases or conditions associated with deregulated angiogenesis, such as acute macular degeneration, age-related macular degeneration, choroidal neovascularisation, retinitis, cytomegalovirus retinitis, macular edema, retinopathy, diabetic retinopathy, neovascular glaucoma and ischemic retinopathy.

In still a further aspect, the invention relates to the use of compounds according to formula I for the manufacture of a medicament for the prophylaxis, treatment or amelioration of skin diseases or conditions associated with deregulated angiogenesis, such as rosacea, psoriasis, dermatitis, squamous cell carcinoma, basal cell carcinoma, malignant melanoma, malignant cutaneous lymphomas, angiosarcoma, Kaposi's sarcoma, proliferating hemangiomas, bullous pemphigoid, erythema multiforme, viral warts, UV-damage and conditions relating to hair growth and cycling and wound healing, optionally comprising another therapeutically active compound.

In still a further aspect, the invention relates to the use of compounds according to formula I for the manufacture of a medicament for the prophylaxis, treatment or amelioration of diseases or conditions associated with deregulated angiogenesis, such as atherosclerosis, haemangioma, haemangioendothelioma, pyogenic granulomas, scar keloids, allergic oedema, dysfunctional uterine bleeding, follicular cysts, ovarian hyperstimulation, endometriosis, obesity, arthritis, rheumatoid arthritis, synovitis, bone and cartilage destruction, osteomyelitis, pannus growth, osteophyte formation, inflammatory and infectious diseases (hepatitis, pneumonia, glomerulonephritis), asthma, nasal polyps, transplantation, liver regeneration, lymphoproliferative disorders, thyroiditis, thyroid enlargement, obstructive lung disease, or cerebral ischaemia reperfusion injury or Alzheimer's disease.

In still a further aspect, the invention relates to the use of compounds according to formula I as an anti-inflammatory agent capable of modulating the activity of a protein tyrosin kinase of the Src family of protein tyrosine kinases.

In still a further aspect, the invention relates to the use of compounds according to formula I as an anti-inflammatory agent capable of modulating the activity of JAK-2 or Raf-1 or cKit or Fma/CSF-1R protein tyrosine kinases.

In still a further aspect, the invention relates to a compound according to formula I for use in the treatment, amelioration or pherophylaxis of non-infectious anti-inflammatory or autoimmune diseases or conditions wherein the non-infectious inflammatory diseases or conditions are selected from the group consisting of acute inflammatory diseases such as acute lung injury, acute respiratory distress syndrome, allergy, anaphylaxis, sepsis or graft-vs-host disease, or chronic inflammatory diseases such as atopic dermatitis, Crohn's disease, ulcerative colitis, osteoarthritis, gout, psoriatic arthritis, hepatic cirrhosis, multiple sclerosis, or ocular diseases or conditions such as non-infectious (e.g. allergic) conjunctivitis, uveitis, iritis, keratitis, scleritis, episcleritis, sympathitic ophthalmitis, blepharitis, keratoconjunctivitis sicca, or immunological cornea graft rejection, and the autoimmune diseases or conditions are selected from the group consisting of autoimmune gastritis, Addison's disease, autoimmune hemolytic anemia, autoimmune thyroiditis, chronic idiopathic urticaria, chronic immune polynephropathy, diabetes, diabetic nephropathy, myasthenia gravis, pemphigus vulgaris, pernicious anemia, primary biliary cirrhosis, systemic lupus erythematosus and thyroid eye disease.

In still a further aspect, the invention relates to intermediates for the preparation of compounds of formula I selected from the group consisting of N-[4-(2,4-Dioxo-4H-benzo[d][1,3]oxazin-1-ylmethyl)-pyridin-2-yl]-acetamide (compound 501);

[4-(2,4-Dioxo-4H-benzo[d][1,3]oxazin-1-ylmethyl)-pyridin-2-yl]-carbamic acid methyl ester (compound 502);

Oxazole-5-carboxylic acid [4-(2,4-dioxo-4H-benzo[d][1,3]oxazin-1-ylmethyl)-pyridin-2-yl]-amide (compound 503);

Furan-2-carboxylic acid [4-(2,4-dioxo-4H-benzo[d][1,3]oxazin-1-ylmethyl)-pyridin-2-yl]-amide (compound 504).

DETAILED DESCRIPTION OF THE INVENTION

Definitions

The term "hydrocarbon radical" is intended to indicate a radical containing only hydrogen and carbon atoms, it may contain one or more double and/or triple carbon-carbon bonds, and it may comprise cyclic moieties in combination with branched or linear moieties. Said hydrocarbon comprises 1-20 carbon atoms, and preferably comprises 1-12 or 1-10 e.g. 1-6, e.g. 1-4, e.g. 1-3, e.g. 1-2 carbon atoms. The term includes alkyl, alkenyl, cycloalkyl, cycloalkenyl, alkynyl and aryl, as indicated below.

In the present context, the term "alkyl" is intended to indicate the radical obtained when one hydrogen atom is removed from a hydrocarbon. Said alkyl comprises 1-20, preferably 1-12, such as 2-6, such as 3-4 carbon atoms. The term includes the subclasses normal alkyl (n-alkyl), secondary and tertiary alkyl, such as methyl, ethyl, n-propyl, isopropyl, n-butyl, isobutyl, sec-butyl, tert-butyl, pentyl, isopentyl, hexyl and isohexyl.

The term "cycloalkyl" is intended to indicate a saturated cycloalkane radical, including polycyclic radicals, such as bicyclic or tricyclic radicals, comprising 3-20 carbon atoms, preferably 3-10 carbon atoms, in particular 3-8 carbon atoms, such as 3-6 carbon atoms, such as 4-5 carbon atoms, e.g. cyclopropyl, cyclobutyl, cyclopentyl, cyclohexyl, cycloheptyl and cyclooctyl.

The term "alkenyl" is intended to indicate a mono-, di-, tri-, tetra- or pentaunsaturated hydrocarbon radical comprising 2-10 carbon atoms, in particular 2-6 carbon atoms, such as 2-4 carbon atoms, e.g. ethenyl, allyl, propenyl, butenyl, pentenyl, nonenyl, or hexenyl.

The term "cycloalkenyl" is intended to indicate mono-, di- tri- or tetraunsaturated non-aromatic cyclic hydrocarbons radicals, including polycyclic radicals, comprising 3-20 carbon atoms, typically comprising 3-10 carbon atoms, such as 3-6 carbon atoms, such as 4-5-carbon atoms, e.g. cyclopropenyl, cyclobutenyl, cyclopentenyl or cyclohexenyl.

The term "alkynyl" is intended to indicate an hydrocarbon radical comprising 1-5 C—C triple bonds and 2-20 carbon atoms, the alkane chain typically comprising 2-10 carbon atoms, in particular 2-6 carbon atoms, such as 2-4 carbon atoms, e.g. ethynyl, propynyl, butynyl, pentynyl or hexynyl.

The term "heterocycloalkyl" is intended to indicate a cycloalkyl radical as defined above, including polycyclic radicals, optionally fused with carbocyclic rings, comprising 1-6 heteroatoms, preferably 1-3 heteroatoms, selected from O, N, or S, e.g. tetrahydrofuranyl, pyrrolidinyl, dioxolanyl, morpholine, imidazolidinyl, or piperidinyl.

The term "heterocycloalkenyl" is intended to indicate a cycloalkenyl radical as defined above, including polycyclic radicals, optionally fused with carbocyclic rings, comprising 1-6 heteroatoms, preferably 1-3 heteroatoms, selected from O, N, or S, e.g. tetrahydropyranol.

The term "aryl" is intended to indicate a radical of aromatic carbocyclic rings comprising 6-20 carbon atoms, such as 6-14 carbon atoms, preferably 6-10 carbon atoms, in particular 5- or 6-membered rings, optionally fused carbocyclic rings with at least one aromatic ring, such as phenyl, naphthyl, anthracenyl, indenyl or indanyl.

The term "heteroaryl" is intended to include radicals of heterocyclic aromatic rings, optionally fused with carbocyclic rings or heterocyclic rings, comprising 1-6 heteroatoms (selected from O, S and N) and 1-20 carbon atoms, such as 1-5 heteroatoms and 1-10 carbon atoms, such as 1-5 heteroatoms and 1-6 carbon atoms, such as 1-5 heteroatoms and 1-3 carbon atoms, in particular 5- or 6-membered rings with 1-4 heteroatoms or 1-2 heteroatoms selected from O, S and N, or optionally fused bicyclic rings with 1-4 heteroatoms, and wherein at least one ring is aromatic, e.g. pyridyl, quinolyl, isoquinolyl, indolyl, tetrazolyl, furyl, thiazolyl, imidazolyl, imidazo[1,2-a]pyrimidinyl, pyrazolyl, oxazolyl, oxadiazolyl, thiophenyl, 1,2,4-triazolyl, isoxazolyl, thienyl, pyrazinyl, pyrimidinyl, [1,2,3]triazolyl, isothiazolyl, imidazo[2,1-b]thiazolyl, benzimidazolyl, benzofuranyl, or benzofuranyl.

The term "carbocyclic" includes aryl, cycloalkanyl, and cycloalkenyl as indicated above.

The term "heterocyclic" includes heteroaryl, heterocycloalkyl, and heterocycloalkenyl as indicated above.

The term "halogen" is intended to indicate a substituent form the $7^{th}$ main group of the periodic table, preferably fluoro, chloro and bromo.

The term "alkylamino" is intended to indicate a radical of the formula —$NR_2$, wherein each R independently represents alkyl, alkenyl or cycloalkyl as indicated above, e.g. methylamino, ethylamino, diethylamino, cyclohexylamino or tert-butylamino.

The term arylamino is intended to indicate a radical of the formula —$NR_2$, wherein R is aryl as indicated above e.g. phenylamino.

The term "alkoxy" is intended to indicate a radical of the formula —OR, wherein R is alkyl or alkenyl as indicated above, e.g. methoxy, ethoxy, n-propoxy, isopropoxy, butoxy, etc.

The term "alkylthio" is intended to indicate a radical of the formula —S—R, wherein R is alkyl as indicated above.

The term "alkoxycarbonyl" is intended to indicate a radical of the formula —C(O)—O—R, wherein R is alkyl as indicated above, e.g. methoxycarbonyl, ethoxycarbonyl, n-propoxycarbonyl, isopropoxycarbonyl, etc.

The term "alkylcarbonyloxy" is intended to indicate a radical of the formula —O—C(O)—R, wherein R is alkyl as indicated above, e.g. methylcarbonyloxy, or ethylcarbonyloxy.

The term "alkylcarbonyl" is intended to indicate a radical of the formula "—C(O)—R, wherein R is alkyl as indicated above, e.g. acetyl.

The term hydroxyalkyl is intended to indicate a radical of the formula —R—OH, wherein R is alkyl as indicated above, e.g. hydroxymethyl or hydroxyethyl.

The term "pharmaceutically acceptable salt" is intended to indicate salts prepared by reacting a compound of formula I with a suitable inorganic or organic acid, such as hydrochloric, hydrobromic, hydroiodic, sulfuric, nitric, phosphoric, formic, acetic, 2,2-dichloroacetic, adipic, ascorbic, L-aspartic, L-glutamic, galactaric, lactic, maleic, L-malic, phthalic, citric, propionic, benzoic, glutaric, gluconic, D-glucuronic, methanesulfonic, salicylic, succinic, malonic, tartaric, benzenesulfonic, ethane-1,2-disulfonic, 2-hydroxy ethanesulfonic acid, toluenesulfonic, sulfamic or fumaric acid. Pharmaceutically acceptable salts of compounds of formula I may also be prepared by reaction with a suitable base such as sodium hydroxide, potassium hydroxide, magnesium hydroxide, calcium hydroxide, silver hydroxide, ammonia or the like.

The term "solvate" is intended to indicate a species formed by interaction between a compound, e.g. a compound of formula I, and a solvent, e.g. alcohol, glycerol or water, wherein said species are in a solid form. When water is the solvent, said species is referred to as a hydrate.

The term "Src" is used to indicate a protein tyrosine kinase of the Src family expressed in a wide range of cells and is inducibly expressed in macrophages. Src is involved in the signal transduction pathways of inflammatory gene expression, for instance mediating TNF-alpha expression in LPS stimulated macrophages.

The term "Yes" is used to indicate a protein tyrosine kinase of the Src family expressed in a wide range of cells. Yes is implicated in the signaling downstream of cytokine signaling in immune and inflammatory cells.

The term "Fyn" is used to indicate a protein tyrosine kinase of the Src family expressed in, i.a., T-cells, B-cells, NK cells and mast cells where it is involved in signaling via the T-cell receptor, adhesion mediated signaling. It has an essential role in mast cell degranulation and cytokine production.

The term "Lck" is used to indicate a protein tyrosine kinase of the Src family expressed in, i.a., T-cells and NK cells where it has a central role in T-cell activation and differentiation.

The term "Lyn" is used to indicate a protein tyrosine kinase of the Src family ubiquitously expressed in hematopoietic cells such as T-cells, B-cells, NK cells, neutrophils, eosinophils, macrophages, monocytes, mast cells and dendritic cells where it is involved, i.a., in modulation of B-cell responses.

The term "Hck" is used to indicate a protein tyrosine kinase of the Src family expressed in, i.a., neutrophils, eosinophils, monocytes, macrophages and dendritic cells where it is involved in transducing a variety of extracellular signals which ultimately affect cellular processes including proliferation, differentiation and migration.

The term "Fgr" is used to indicate a protein tyrosine kinase of the Src family expressed in, i.a., neutrophils, eosinophils, monocytes, macrophages and dendritic cells where it is involved in the signaling cascade from the B-cell receptor, FcR and the integrin family of receptors.

The term "Jak-2" is used to indicate a protein tyrosine kinase of the JAK (Janus protein tyrosine kinase) family highly expressed in immune cells where it is essential for signaling downstream of many cytokines and growth factors including the proinflammatory cytokines IL-6, IFN-γ, IL-3, IL-5 and GM-CSF.

The term "cKit" is used to indicate a receptor tyrosine kinase which is the receptor for stem cell factor (SCF) and is required for normal hematopoiesis. cKit plays an essential role in mast cell function as SCF is necessary for mast cell development, proliferation and survival. SCF is essential for optimal IgE/antigen-induced mast cell degranulation and cytokine production. Activation of c-kit induces eosinophil activation and degranulation.

The term "Fms/CSF-1R" is used to indicate a receptor tyrosine kinase which is the receptor for CSF-1 and is primarily expressed by monocytes and macrophages. CSF-1 plays a central role in macrophage effector functions during inflammation and regulates macrophage differentiation, survival and function.

The term "Raf-1" is used to indicate a tyrosine kinase-like serine/threonine kinase of the RAF family members of which are the main effectors recruited by GTP-bound Ras to activate the MEK-MAP kinase pathway. This pathway has been implicated in the expression of the proinflammatory cytokine GM-CSF and in the development of chronic inflammation by interfering with the longevity of neutrophils.

PREFERRED EMBODIMENTS OF COMPOUNDS OF FORMULA I

In a currently preferred embodiment of the invention W represents oxygen.

In another preferred embodiment of the invention, Y is C(O).

In another preferred embodiment of the invention $R_1$ represents hydrogen or methyl.

In yet another embodiment of the invention, $R_2$ is hydrogen or methyl.

In yet another embodiment of the invention, $R_3$ is hydrogen or methyl.

In another preferred embodiment of the invention $R_1$ represents hydrogen.

In yet another embodiment of the invention, $R_2$ is hydrogen.

In yet another embodiment of the invention, $R_3$ is hydrogen.

In yet another embodiment of the invention, $R_1$, $R_2$ and $R_3$ each represent hydrogen.

In yet another preferred embodiment of the invention D is CH.

In yet another preferred embodiment of the invention E is CH.

In yet another preferred embodiment of the invention G is CH.

In yet another preferred embodiment of the invention J is CH.

In yet another preferred embodiment of the invention L is CH.

In yet another embodiment of the invention, n is 1.

In yet another preferred embodiment of the invention, W represents oxygen, Y is C(O), $R_1$, $R_2$ and $R_3$ each represent hydrogen, CH and n is 1.

In yet another preferred embodiment of the invention, D is CH, E is CH, G is CH, and J is CH.

In yet another preferred embodiment of the invention, D is nitrogen, E is CH, G is CH, and J is CH.

In yet another preferred embodiment of the invention, $R_4$ is $C_{1-6}$alkyl, $C_{2-6}$alkenyl, $C_{2-6}$alkynyl, $C_{1-4}$hydroxyalkyl, $C_{3-6}$cycloalkyl, $C_{3-6}$cycloalkenyl, $C_{2-5}$heterocycloalkyl, $C_{2-5}$heterocycloalkenyl, $C_{6-12}$aryl or $C_{6-12}$heteroaryl, wherein said $C_{1-6}$alkyl, $C_{2-6}$alkenyl, $C_{2-6}$alkynyl, $C_{1-4}$hydroxyalkyl, $C_{3-6}$cycloalkyl, $C_{3-6}$cycloalkenyl, $C_{2-5}$heterocycloalkyl, $C_{2-5}$heterocycloalkenyl, $C_{6-12}$aryl or $C_{6-12}$heteroaryl, are optionally substituted by one or more, same or different substituents independently selected from the group consisting of hydrogen, fluoro, hydroxy, trifluoromethyl, cyano, $C_{1-4}$alkyl, $C_{2-4}$alkenyl, $C_{1-4}$alkoxy, $C_{1-4}$alkylthio, $C_{3-6}$cycloalkyl, $C_{3-6}$cycloalkenyl, $C_{2-5}$heterocycloalkyl, $C_{2-5}$heterocycloalkenyl and $C_{1-3}$alkylamino wherein said $C_{1-4}$alkyl, $C_{2-4}$alkenyl, $C_{1-4}$alkoxy, $C_{1-4}$alkylthio, $C_{3-6}$cycloalkyl, $C_{3-6}$cycloalkenyl, $C_{2-5}$heterocycloalkyl, $C_{2-5}$heterocycloalkenyl and $C_{1-3}$alkylamino are optionally substituted by one or more, same or different substituents independently selected from hydroxy, methyl, ethyl, methoxycarbonyl, ethoxycarbonyl.

Preferably, the group represented by $R_4$ comprises between 1 and 10 carbon atoms. More preferably, the group represented by $R_4$ comprises from 3 to 8 carbon atoms.

In yet another preferred embodiment of the invention, $R_4$ is $C_{1-6}$alkyl, $C_{2-6}$alkenyl, $C_{3-6}$cycloalkyl, $C_{3-6}$cycloalkenyl, $C_{2-5}$heterocycloalkyl, $C_{2-5}$heterocycloalkenyl, wherein said $C_{1-6}$alkyl, $C_{2-6}$alkenyl, $C_{3-6}$cycloalkyl, $C_{3-6}$cycloalkenyl, $C_{2-5}$heterocycloalkyl, $C_{2-5}$heterocycloalkenyl, are optionally substituted by one or more, same or different substituents independently selected from the group consisting of hydrogen, $C_{1-4}$alkyl, $C_{2-4}$alkenyl, $C_{3-6}$cycloalkyl, and $C_{3-6}$cycloalkenyl, wherein said $C_{1-4}$alkyl, $C_{2-4}$alkenyl, $C_{3-6}$cycloalkyl and $C_{3-6}$cycloalkenyl are optionally substituted by one or more, same or different substituents independently selected from methyl and ethyl.

In another preferred embodiment, $R_4$ contains no more than 3 heteroatoms, more preferably no more than 1 heteroatom and most preferably consists of only carbon and hydrogen atoms.

In yet another preferred embodiment of the invention, $R_4$ is isobutyl, isopentyl, methylbutyl, ethylbutyl, tert-butyl, tert-butylmethyl, hydroxyethyl, hydroxyisobutyll, ethylhydroxybutyl, methoxymethyl, methoxyethyl, ethylthiomethyl, fluoromethyl, trifluoroethyl, cyanomethyl, diethylaminomethyl, cyclopropyl, cyclopropylmethyl, ethoxycarbonylcyclopropyl, cyclobutyl, cyclobutylmethyl, cyclobutylethyl, cyclopentyl, cyclopentylmethyl, cyclopentylhydroxymethyl, cyclopentylethyl, cyclohexyl, cyclohexylmethyl, cyclohexenylmethyl, tetrahydrofuranylmethyl, tetrahydropyranyl, tetrahydropyranyl, tetrahydropyranylmethyl, dimethyldioxolanyl, pyrrolidinylmethyl, furfuryl, thienyl, thienylmethyl, phenyl, benzyl, phenylethyl, phenylhydroxymethyl, pyridylmethyl.

In yet another preferred embodiment of the invention, $R_4$ is cyclopentylmethyl, 2-ethyl-butyl, 3-methyl-butyl, t-butylmethyl or cyclohex-1-enylmethyl.

In yet another preferred embodiment of the invention, $R_3$ and $R_4$ form part of a cyclopropyl, cyclobutyl, cyclopentyl or cyclohexyl ring.

In yet another preferred embodiment of the invention, $R_5$ represents hydrogen, methyl, ethyl, propyl, $C_{1-3}$alkylamino, methoxy, ethoxy, $C_{3-6}$cycloalkyl, $C_{4-6}$cycloalkenyl, $C_{2-5}$heterocycloalkyl or $C_{2-5}$heteroaryl, wherein said methyl, ethyl, propyl, $C_{1-3}$alkylamino, methoxy, ethoxy, $C_{3-6}$cycloalkyl, $C_{4-6}$cycloalkenyl, $C_{2-5}$heterocycloalkyl or $C_{2-5}$heteroaryl are optionally substituted with one or more substituents independently selected from the group consisting of cyano, methyl, ethyl, propyl, methoxycarbonyl, ethoxycarbonyl, propoxycarbonyl, methylcarbonyloxy or ethylcarbonyloxy.

In yet another preferred embodiment of the invention, $R_5$ represents hydrogen, methyl, methylamino, ethylamino, methoxy, ethoxy, cyanomethyl, cyclopropyl, methoxycarbonylethyl, methylcarbonyloxymethyl, tetrahydrofuranyl, furyl, thienyl, isoxazolyl, oxazolyl, thiazole, oxadiazolyl, thiadiazolyl or triazolyl, all of which are optionally substituted with methyl.

In yet another embodiment of the invention, $R_5$ has a molecular weight no greater than 100 Daltons.

In yet another embodiment, $R_5$ comprises no more than 5 carbon atoms.

In yet another embodiment of the invention, $R_5$ is methyl, furyl, methoxy or oxazolyl.

In yet another preferred embodiment of the invention, the compound of formula I is selected from the group consisting of (4-{[2-(3,3-Dimethyl-butylcarbamoyl)-phenylamino]-methyl}-pyridin-2-yl)-carbamic acid methyl ester (compound 101);

2-[(2-Acetylamino-pyridin-4-ylmethyl)-amino]-N-(2-cyclopentyl-ethyl)-benzamide (compound 102);

2-[(2-Acetylamino-pyridin-4-ylmethyl)-amino]-N-(3-ethyl-pentyl)-benzamide (compound 103);

Oxazole-5-carboxylic acid (4-{[2-(3-ethyl-pentylcarbamoyl)-phenylamino]-methyl}-pyridin-2-yl)-amide (compound 104);

Furan-2-carboxylic acid (4-{[2-(2-cyclopentyl-ethylcarbamoyl)-phenylamino]-methyl}-pyridin-2-yl)-amide (compound 105);

Furan-2-carboxylic acid (4-{[2-(4-methyl-pentylcarbamoyl)-phenylamino]-methyl}-pyridin-2-yl)-amide (compound 106);

Furan-2-carboxylic acid (4-{[2-(3,3-dimethyl-butylcarbamoyl)-phenylamino]-methyl}-pyridin-2-yl)-amide (compound 107);

Furan-2-carboxylic acid (4-{[2-(2-cyclohex-1-enyl-ethylcarbamoyl)-phenylamino]-methyl}-pyridin-2-yl)-amide (compound 108);

Furan-2-carboxylic acid (4-{[2-(3-ethyl-pentylcarbamoyl)-phenylamino]-methyl}-pyridin-2-yl)-amide (compound 109).

In yet another presently preferred embodiment the compounds of general formula I have a molecular weight below 1300 Dalton, such as below 900 Dalton, e.g. below 800 Dalton, e.g. below 700 Dalton, e.g. below 600 Dalton, e.g. below 500 Dalton.

In yet another preferred embodiment the pharmaceutical compositions may further comprise another therapeutically active compound.

The compounds of formula I may be obtained in crystalline form either directly by concentration from an organic solvent or by crystallisation or recrystallisation from an organic solvent or mixture of said solvent and a cosolvent that may be organic or inorganic, such as water. The crystals may be isolated in essentially solvent-free form or as a solvate, such as a hydrate. The invention covers all crystalline modifications and forms and also mixtures thereof.

Compounds of formula I may comprise asymmetrically substituted (chiral) carbon atoms and carbon-carbon double bonds which may give rise to the existence of isomeric forms, e.g. enantiomers, diastereomers and geometric isomers. The present invention relates to all such isomers, either in pure form or as mixtures thereof. The invention also relates to all possible tautomers of the compounds of formula I.

Formation of new blood vessels takes place in a balance between factors working for and against this formation, i.e. in a balance between pro-angiogenic and anti-angiogenic compounds. Early in development, proliferating and differentiating endothelial cells form vessels in previously avascular tissue. This first stage is a leaky network which has to be remodelled to reach a mature vessel. This process is referred to as vasculogenesis. Formation of a new blood vessel may also occur from an already existing blood vessel in a process referred to as angiogenic sprouting. Here, the "old" vessel is initially destabilised at a located site, and the new vessel is formed from there and is subsequently matured.

The processes above commonly involve the vascular endothelial, which is a particular type of endothelium composed by a single layer of smooth cells that cover the lumen of blood vessels. A number of specific growth factors acting on said endothelial have been identified, and they include five members of the vascular endothelial growth factor (VEGF) family, four members of the angiopoietin family, and one member of the large ephrin family. VEGF, however, holds the position as the most critical driver of vascular formation as it is required to initiate the formation of immature vessels both by vasculogenesis and angiogenic sprouting [Yancopoulos, Nature, 407, 242-248, 2000]. VEGF, originally termed "Vascular Permeability Factor" (VPF) is the angiogenic factor which lies at the centre of the network regulating the growth and differentiation of the vascular system and its components during embryonic development, normal growth and in a wide number of pathological anomalies along with its cellular receptors [G. Breier et al., Trends in Cell Biology 6, 454-6, 1996].

VEGF is a dimeric, disulfide-linked 46-kDa glycoprotein related to "Platelet-Derived Growth Factor" (PDGF); it is produced by normal cell lines and tumour cell lines; it is an endothelial cell-specific mitogen; shows angiogenic activity in in vivo test systems (e.g. rabbit cornea); is chemotactic for endothelial cells and monocytes; and induces plasminogen activators in endothelial cells, which are involved in the proteolytic degradation of extracellular matrix during the formation of capillaries. A number of isoforms of VEGF are known, which show comparable biological activity, but differ in the type of cells that secrete them and in their heparin-binding capacity. In addition, there are other members of the VEGF family, such as "Placenta Growth Factor" (PlGF) and VEGF-C.

VEGFs are unique in that they are the only angiogenic growth factors known to contribute to vascular hyperpermeability and the formation of edema. Indeed, vascular hyperpermeability and edema that is associated with the expression or administration of many other growth factors appears to be mediated via VEGF production.

Inflammatory cytokines stimulate VEGF production. Hypoxia results in a marked upregulation of VEGF in numerous tissues, hence situations involving infarct, occlusion, ischemia, anemia, or circulatory impairment typically invoke VEGF/VPF-mediated responses, Vascular hyperpermeability, associated edema, altered transendothelial exchange and macromolecular extravasation, which is often accompanied by diapedesis, can result in excessive matrix deposition, aberrant stromal proliferation, fibrosis, etc. Hence, VEGF-mediated hyperpermeability can significantly contribute to disorders with these etiologic features. As such, regulators of angiogenesis have become an important therapeutic agent.

Three VEGF receptors are known, VEGFR-1 (or fms-like tyrosine kinase receptor (Flt-1)), VEGFR-2 and VEGFR-3, and they are expressed almost exclusively on endothelial cells. VEGFR-2 was previously referred to as KDR (kinase insert domain-containing receptor), and this receptor appears to play a crucial role in the induction of cell proliferation by VEGF [Ellis, *Seminars in Oncology*, 28, 94-104, 2001]. The VEGF receptors belong to the group of tyrosine kineasereceptors, and they are composed of seven extracellular Ig-like domains, harbouring the VEGF binding site, and an intracellular tyrosine kinase domain. The intra- and extracellular domains are connected by a short transmembrane segment [Shawver, *DDT*, 2, 50-63, 1997]. Like other receptor tyrosine kinases, VEGFR-2 dimerise upon binding to VEGF, and the tyrosine kinase domain becomes autophosphorylated. This activated form, in turn, binds to other molecules which are activated, e.g. by yet another phosphorylation. This cascade eventually triggers the proliferation of endothelial cells, and thus the formation of new blood vessels.

Whilst blood vessels in healthy adults are largely quiescent, adult skin retains the capacity for rapid initiation of angiogenesis during tissue repair and in numerous diseases including inflammatory skin diseases such as psoriasis, many types of dermatitis, blistering diseases, cutaneous neoplasias including squamous cell carcinomas, malignant melanomas, and Kaposi's sarcomas, and proliferative hemangiomas of childhood. Angiogenesis in the skin is also implicated in a number of other diseases that are characterised by macroscopically visible, prominent blood vessels, including rosacea and basal cell carcinoma. The compounds of the present invention would be particularly useful for the treatment of each of these.

Research has suggested that in normal skin, vascular quiescence is maintained by the influence of endogenous angiogenesis inhibitors, which outweighs the influence of angiogenic stimuli. Angiogenesis may, therefore, be caused by increased secretion of angiogenic factors or the downregulation of angiogenesis inhibitors.

Vascular endothelial growth factor is a key angiogenic factor implicated in diseases relating to increased angiogenesis in the skin. In normal skin, it has been found that VEGF is expressed at low levels, whereas in skin diseases associated with angiogenesis, including psoriasis, contact dermatitis, several bullous diseases, viral papillomas and squamous cell carcinoma, there is prominent upregulation of VEGF expression by epidermal keratinocytes.

A more detailed discussion of the role of VEGF in skin angiogenesis is given by Detmar in *Journal of Dermatological Science* 24 Suppl. 1 (2000); 78-84.

Of particular interest in the present invention is rosacea. Rosacea is a common condition characterised by inflammation and vascular abnormalities of the facial skin and eyes. Erythema and blushing can develop from transient to persistent and are often accompanied by telangiectasis or papules and pustules. In some cases there may be a thickening of the nose tissue as a result of persistent edema. In most cases, only some of these features are present and this has lead to the need to split the broad umbrella of rosacea into sub-classes. This is especially important, because often treatments that are very effective for patients suffering from one type of rosacea may be far less effective for others. Rosacea has been divided into four sub-types: erythematelangiectatic type, papulopustular, phymatous and ocular (see Crawford G H et al. J Am Acad Dermatol 2004; 51: 327-41).

The role of VEGF in rosacea has been explored by Gomaa A H A et al. (J Cutan Pathol 2007; 34: 748-753) and Smith J R et al. (Br J Opthalmol 2007; 91: 226-229), the latter finding increased expression of dermal VEGF in lesional cutaneous specimens from patients with non-phymatous rosacea and suggesting that VEGF may be causally related to increased angiogenesis in non-phymatous rosacea.

Compounds of the present invention would, therefore, be useful for the treatment of rosacea, particularly non-phymatous rosacea.

As discussed below, the majority of human cancers are characterised by overexpression of VEGF by tumour cells and by overexpression of VEGF receptors on blood vessels associated with the tumour. VEGF also appears to affect very early tumour development in squamous cell carcinomas of the skin. VEGF-C also acts at the VEGFR-2 as well as at VEGFR-3 and its expression is thought to be key in Kaposi's sarcomas.

Tumour cells require oxygen to grow and to metastasize. Oxygen has a very limited diffusion range, so for the tumour to grow beyond a very limited size, they cannot rely on passive oxygen transport, but rather they have to establish an active oxygen transport, i.e. they have to attract blood vessels from the host. Nutrients, required by the tumour, are also supplied through the blood vessels. A tumour will start in or eventually expand into an avascular area resulting in low $pO_2$ and pH, and these factors trigger an upregulation of, e.g. VEGF in the tumour cells. Without sufficient oxygen and nutrient supply, the tumour cells become necrotic or apoptotic, and the tumour will thus cease to grow, and may even regress. Angiogenesis is regarded as an absolute prerequisite for tumours which grow beyond a diameter of about 1-2-mm; up to this limit, oxygen and nutrients may be supplied to the tumour cells by diffusion. Every tumour, regardless of its origin and its cause, is thus dependent on angiogenesis for its growth after it has reached a certain size. A large number of human tumours, especially gliomas and carcinomas, express high levels of VEGF. This has led to the hypothesis that the VEGF released by tumor cells stimulates the growth of blood capillaries and the proliferation of tumour endothelium in a paracrine manner and through improved blood supply, accelerate tumour growth. Increased VEGF expression could explain the occurrence of cerebral edema in patients with glioma. Direct evidence of the role of VEGF as a tumour angiogenesis factor in vivo is shown in studies in which VEGF expression or VEGF activity was inhibited. This was achieved with anti-VEGF antibodies, with dominant-negative VEGFR-2 mutants which inhibited signal transduction, and with antisense-VEGF RNA techniques. All approaches led to a reduction in the growth of glioma cell lines or other tumour cell lines in vivo as a result of inhibited tumour angiogenesis. Already in 1971 Folkman suggested that inhibition of angiogenesis could be a strategy for treating cancers which are manifested by solid tumours [Folkman, in Cancer Medicine, (Eds Holland et al), 132-152, Decker Ontario, Canada, 2000]. This notion was based on even earlier observations that angiogenesis occurs around tumours, and on hypotheses that an "angiogenic" principle was produced by the tumours.

Three principal mechanisms play an important part in the activity of angiogenesis inhibitors against tumours: 1) inhibition of the growth of vessels, especially capillaries, into vascular resting tumours, with the result that there is no net tumour growth owing to the balance that is achieved between apoptosis and proliferation; 2) prevention of the migration of tumour cells owing to the absence of blood flow to and from tumours; and 3) inhibition of endothelial cell proliferation, thus avoiding the paracrine growth-stimulating effect exerted on the surrounding tissue by the endothelial cells which normally line the vessels [R. Connell et al., Exp. Opin. Ther. Patents, 11, 77-114, 2001]. As mentioned above, the compounds of the present invention inhibit VEGFR-2 (KDR), and therefore prevent angiogenesis, i.e. the formation of new blood vessels, and they will thus cause the tumour to cease growing and perhaps even to regress.

Compounds of the invention would be useful for the prophylaxis, treatment or amelioration of a disease or condition associated with deregulated angiogenesis, such as the prophylaxis, treatment or amelioration of tumours or neoplastic diseases such as squamous cell carcinoma, basal cell carcinoma, malignant melanoma, malignant cutaneous lymphomas, angiosarcoma, Kaposi's sarcoma and proliferating hemangiomas.

A number of eye diseases are also related to the process of angiogenesis, for instance proliferative diabetic retinopathy, retinopathy of prematurity, rubeosis iridis and secondary glaucoma after branch and central retinal vein occlusion, age-related maculopathy and corneal neovascularisation. Whilst the complex system of angiogenic regulation is not yet fully understood, increased levels of VEGF have been linked to a number of these conditions. It is known that tissue hypoxia and inflammation can stimulate its secretion and increased levels of VEGF mRNA, probably regulated by oxygen-sensing haem proteins, have been found in hypoxic areas of the detached retina. In diabetic retinopathy too, hypoxic nonperfused areas of the retina secrete VEGF, which appears to be the most important factor in this condition.

The cells of the capillary wall (endothelial cells, pericytes and smooth muscle cells) in the retina along with Müller cells and retinal pigment epithelial cells can all secrete VEGF and VEGF receptors are found in high concentrations on ocular endothelial cells. The VEGF might act locally in the retina (for example as in proliferative diabetic vitreoretinopathy) or diffuse to the anterior segment (where it can cause rubeosis iridis or rubeosis of the iridocorneal angle). As well as causing angiogenesis, VEGF also has the effect of increasing vascular permeability and so is implicated in inflammatory diseases associated with angiogenesis, in which there is breakdown of the blood-retina barrier.

There are four potential targets for inhibition of VEGF. These are to inhibit VEGF secretion, to inactivate VEGF, to block VEGF receptors on ocular endothelial cells and to inhibit postsynaptic VEGF induced cell activation. The present invention is concerned with blocking VEGF receptors, in particular VEGFR-2.

However, due to the complex nature of angiogenic signalling pathways and the large number of angiogenic factors, blocking a single factor or receptor might not be sufficient to achieve a reduction of angiogenesis. Therefore, the compounds of the present invention are suitable for use in conjunction with other anti-angiogenic compounds, especially those that target different parts of the angiogenic regulation system.

The role of angiogenesis and VEGF in ocular diseases is discussed in further detail by Cursiefen and Schönherr in *Klin Monatsbl Augenheilkd* 1997; 210: 341-351.

Deregulated angiogenesis has been implicated in a large variety of pathological conditions or diseases (see P. Carmeliet & R. K. Jain, Nature, Vol. 407, 2000, pp. 249-257; A. H. Vagnucci & W. W. Li, The Lancet, Vol. 361, 2003, 605-608; B. Xuan et al., J. Ocular Pharmacology & Therapeutics, Vol. 15(2), 1999, pp. 143-152). Compounds of the present invention would be useful for, but are not limited to the prevention, prophylaxis, treatment or amelioration of a disease or condition associated or related with deregulated angiogenesis. These conditions or diseases include conditions or diseases charaterised by abnormal angiogenesis or vascular malfunction, rosacea, atherosclerosis, haemangioma, haemangioendothelioma, warts, pyogenic granulomas, hair growth, scar keloids, allergic oedema, dysfunctional uterine bleeding, follicular cysts, ovarian hyperstimulation, endometriosis, obesity, arthritis, rheumatoid arthritis, synovitis, bone and cartilage destruction, osteomyelitis, pannus growth, osteophyte formation, inflammatory and infectious diseases (hepatitis, pneumonia, glomerulonephritis), asthma, nasal polyps, transplantation, liver regeneration, retinopathy, diabetic retinopathy, neovascular glaucoma, endometriosis, psoriasis, lymphoproliferative disorders, thyroiditis, thyroid enlargement, obstructive lung disease, or cerebral ischaemia reperfusion injury, Alzheimer's disease, and eye diseases such as acute macular degeneration, age-related macular degeneration, choroidal neovascularisation, retinitis, cytomegalovirus retinitis, macular edema and ischemic retinopathy.

Compounds of formula I are currently believed to be useful as inhibitors of other kinases as well such as protein tyrosine kinases of the Src family such as Src, Yes, Fyn, Lyn, Fgr, Lck and/or Hck, and/or JAK-2, and/or Raf-1, and/or cKit, and/or Fma/CSF-1R protein tyrosine kinases and are therefore believed to be useful in the treatment, amelioration or prophylaxis of non-infectious inflammatory or autoimmune diseases or conditions wherein these kinases are involved.

Examples of such non-infectious inflammatory diseases or conditions are selected from the group consisting of acute inflammatory diseases such as acute lung injury, acute respiratory distress syndrome, allergy, anaphylaxis, sepsis or graft-vs-host disease, or chronic inflammatory diseases such as atopic dermatitis, Crohn's disease, ulcerative colitis, osteoarthritis, gout, psoriatic arthritis, hepatic cirrhosis or multiple sclerosis.

Examples of such autoimmune diseases are selected from the group consisting of autoimmune gastritis, Addison's disease, autoimmune hemolytic anemia, autoimmune thyroiditis, chronic idiopathic urticaria, chronic immune polynephropathy, diabetes, diabetic nephropathy, myasthenia gravis, pemphigus vulgaris, pernicious anemia, primary biliary cirrhosis, systemic lupus erythematosus and thyroid eye disease.

Compounds of formula I are currently believed to be particularly useful in the treatment of non-infectious inflammatory ocular diseases or conditions such as non-infectious (e.g. allergic) conjunctivitis, uveitis, iritis, keratitis, scleritis, episcleritis, sympathitic ophthalmitis, blepharitis, keratoconjunctivitis sicca, or immunological cornea graft rejection.

Besides being useful for human treatment, the compounds of the present invention may also be useful for veterinary treatment of animals including mammals such as horses, cattle, sheep, pigs, dogs, and cats.

For use in therapy, compounds of the present invention are typically in the form of a pharmaceutical composition or pharmaceutical formulation. The invention therefore relates to a pharmaceutical composition comprising a compound of formula I, optionally together with one or more other therapeutically active compounds, such as differentiating agents such as vitamin D derivatives and all-trans retinoid acid; corticosteroids, such as dexamethasone and prednisone, chemotherapeutic agents, anticancer agents, cytotoxic agents, together with a pharmaceutically acceptable excipient or vehicle. The excipient must be "acceptable" in the sense of being compatible with the other ingredients of the composition and not deleterious to the recipient thereof.

If the treatment involves administration of another therapeutically active compound it is recommended to consult *Goodman & Gilman's The Pharmacological Basis of Therapeutics*, $9^{th}$ Ed., J. G. Hardman and L. E. Limbird (Eds.), McGraw-Hill 1995, for useful dosages of said compounds.

Conveniently, the active ingredient comprises from 0.1-99.9% by weight of the composition.

By the term "dosage unit" is meant a unitary, i.e. a single dose which is capable of being administered to a patient, and which may be readily handled and packed, remaining as a physically and chemically stable unit dose comprising either the active material as such or a mixture of it with solid or liquid pharmaceutical diluents or carriers. In the form of a dosage unit, the compound may be administered one or more times a day at appropriate intervals, always depending, however, on the condition of the patient, and in accordance with the prescription made by the medical practitioner. It is also envisaged that in certain treatment regimes, administration with longer intervals e.g. every other day, every week, or even with longer intervals may be beneficial.

Conveniently, dosage unit of a formulation contains between 0.01 mg and 10000 mg, preferably between 100 mg and 3000 mg, such as between 200 mg and 1000 mg of a compound of formula I.

The formulations include e.g. those in a form suitable for ophthalmic (including sustained or time-released), oral (including sustained or timed release), rectal, parenteral (including subcutaneous, intraperitoneal, intramuscular, intraarticular and intravenous), transdermal, topical, nasal or buccal administration.

The formulations may conveniently be presented in dosage unit form and may be prepared by any of the methods well known in the art of pharmacy, e.g. as disclosed in Remington, *The Science and Practice of Pharmacy*, $20^{th}$ ed., 2000. All methods include the step of bringing the active ingredient into association with the carrier, which constitutes one or more accessory ingredients. In general, the formulations are prepared by uniformly and intimately bringing the active ingredient into association with a liquid carrier or a finely divided solid carrier or both, and then, if necessary, shaping the product into the desired formulation.

Formulations suitable for ophthalmic administration may be in the form of a sterile aqueous preparation of the active ingredients, which may be in microcrystalline form, for example, in the form of an aqueous microcrystalline suspension. Liposomal formulations or biodegradable polymer systems e.g. as disclosed in Encyclopedia of Pharmaceutical Technology, vol. 2, 1989, may also be used to present the active ingredient for ophthalmic administration.

Formulations suitable for topical or ophthalmic administration include liquid or semi-liquid preparations such as liniments, lotions, gels, applicants, oil-in-water or water-in-oil emulsions such as creams, ointments or pastes; or solutions or suspensions such as drops, intravitreal injection and time-released drug systems.

Formulations of the present invention suitable for oral administration may be in the form of discrete units as capsules, sachets, tablets or lozenges, each containing a predetermined amount of the active ingredient; in the form of a powder or granules; in the form of a solution or a suspension in an aqueous liquid or non-aqueous liquid, such as ethanol or glycerol; or in the form of an oil-in-water emulsion or a water-in-oil emulsion. Such oils may be edible oils, such as e.g. cottonseed oil, sesame oil, coconut oil or peanut oil. Suitable dispersing or suspending agents for aqueous suspensions include synthetic or natural gums such as tragacanth, alginate, acacia, dextran, sodium carboxymethylcellulose, gelatin, methylcellulose, hydroxypropylmethylcellulose, hydroxypropylcellulose, carbomers and polyvinylpyrrolidone. The active ingredients may also be administered in the form of a bolus, electuary or paste.

A tablet may be made by compressing or moulding the active ingredient optionally with one or more accessory ingredients. Compressed tablets may be prepared by compressing, in a suitable machine, the active ingredient(s) in a free-flowing form such as a powder or granules, optionally mixed by a binder, such as e.g. lactose, glucose, starch, gelatine, acacia gum, tragacanth gum, sodium alginate, carboxymethylcellulose, methylcellulose, hydroxypropylmethylcellulose, polyethylene glycol, waxes or the like; a lubricant such as e.g. sodium oleate, sodium stearate, magnesium stearate, sodium benzoate, sodium acetate, sodium chloride or the like; a disintegrating agent such as e.g. starch, methylcellulose, agar, bentonite, croscarmellose sodium, sodium starch glycollate, crospovidone or the like or a dispersing agent, such as polysorbate 80. Moulded tablets may be made by moulding, in a suitable machine, a mixture of the powdered active ingredient and suitable carrier moistened with an inert liquid diluent.

Formulations for rectal administration may be in the form of suppositories in which the compound of the present invention is admixed with low melting water soluble or insoluble solids such as cocoa butter, hydrogenated vegetable oils, polyethylene glycol or fatty acids esters of polyethylene glycols, while elixirs may be prepared using myristyl palmitate.

Formulations suitable for parenteral administration conveniently comprise a sterile oily or aqueous preparation of the active ingredients, which is preferably isotonic with the blood of the recipient, e.g. isotonic saline, isotonic glucose solution or buffer solution. The formulation may be conveniently sterilised by for instance filtration through a bacteria retaining filter, addition of sterilising agent to the formulation, irradiation of the formulation or heating of the formulation. Liposomal formulations as disclosed in e.g. Encyclopedia of Pharmaceutical Technology, vol. 9, 1994, are also suitable for parenteral administration.

Alternatively, the compound of formula I may be presented as a sterile, solid preparation, e.g. a freeze-dried powder, which is readily dissolved in a sterile solvent immediately prior to use.

Transdermal formulations may be in the form of a plaster or a patch.

Formulations suitable for nasal or buccal administration include powder, self-propelling and spray formulations, such as aerosols and atomisers. Such formulations are disclosed in greater detail in e.g. *Modern Pharmaceutics*, $2^{nd}$ ed., G. S. Banker and C. T. Rhodes (Eds.), page 427-432, Marcel Dekker, New York; *Modern Pharmaceutics*, $3^{th}$ ed., G. S. Banker and C. T. Rhodes (Eds.), page 618-619 and 718-721, Marcel Dekker, New York and *Encyclopedia of Pharmaceutical Technology* vol. 10, J Swarbrick and J. C. Boylan (Eds), page 191-221, Marcel Dekker, New York.

In addition to the aforementioned ingredients, the formulations of a compound of formula I may include one or more additional ingredients such as diluents, buffers, flavouring agents, colourant, surface active agents, thickeners, preservatives, e.g. methyl hydroxybenzoate (including anti-oxidants), emulsifying agents and the like.

When the active ingredient is administered in the form of salts with pharmaceutically acceptable non-toxic acids or bases, preferred salts are for instance easily water-soluble or slightly soluble in water, in order to obtain a particular and appropriate rate of absorption.

Methods of Preparation

The compounds of the present invention can be prepared in a number of ways well known to those skilled in the art of organic synthesis. The compounds of the present invention can be synthesised using the methods outlined below, together with methods known in the art of synthetic organic chemistry, or variations thereof as appreciated by those skilled in the art. Preferred methods include, but are not limited to, those described below.

The novel compounds of formula (I) may be prepared using the reactions and techniques described in this section. The reactions are performed in solvents appropriate to the reagents and materials employed and suitable for the transformations being effected. Also, in the synthetic methods described below, it is to be understood that all proposed reaction conditions, including choice of solvent, reaction atmosphere, reaction temperature, duration of experiment and work-up procedures, are chosen to be conditions of standard for that reaction, which should be readily recognised by one skilled in the art. It is understood by one skilled in the art of organic synthesis that the functionality present on various portions of the starting molecule in a reaction must be compatible with the reagents and reactions proposed. Not all compounds of formula (I) falling into a given class may be compatible with some of the reaction conditions required in some of the methods described. Such restrictions to the substituents which are compatible with the reaction conditions will be readily apparent to one skilled in the art and alternative methods can be used.

The compounds of formula (I) can be prepared by techniques and procedures readily available to one skilled in the art, for example by following the procedures as set forth in the following Schemes. These Schemes are not intended to limit the scope of the invention in any way. All substituents, unless otherwise indicated, are previously defined. The reagents and starting materials are readily available to one skilled in the art.

The compounds of formula (I) are generally obtained by reacting a compound of formula (II) with an amine of formula (III) as shown in Scheme 1. Preferred solvents are aprotic solvents such as DMF and pyridine.

The reactions are generally carried out at a temperature between about −78° C. to about 60° C., often at about room temperature and are normally complete within about 2 hours to about 5 days. Filtration and evaporation of the solvent under reduced pressure affords the products that may be further purified, if desired, by standard methods such as chromatography, crystallisation, or distillation. Alternatively, the products can be isolated by removing the solvent used to perform the reaction in, for example by evaporation under reduced pressure and further purified as mentioned above.

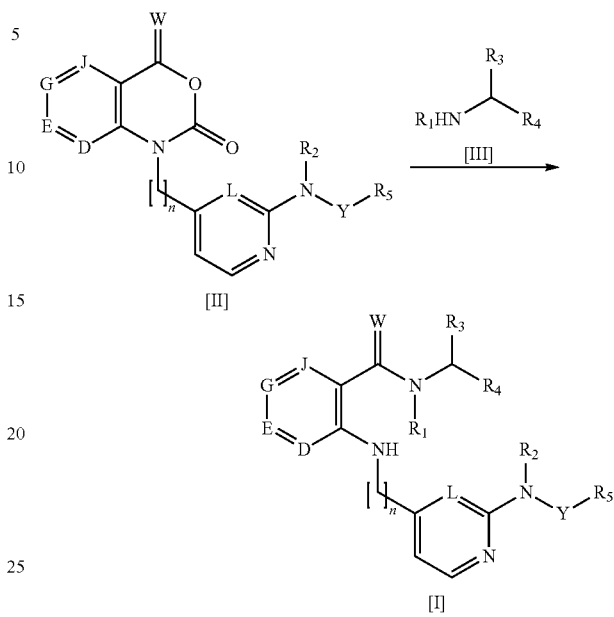

Scheme 1: General method for the preparation of compounds of general formula (I) from compounds of general formula (II).

Compounds of the general formula (II) are generally prepared by reacting an amine of the general formula (IV) with a compound of formula (V). Preferred solvents are aprotic solvents such a pyridine.

The reactions are generally carried out at a temperature between about −78° C. to about 60° C., often at about room temperature and are normally complete within about 2 hours to about 5 days.

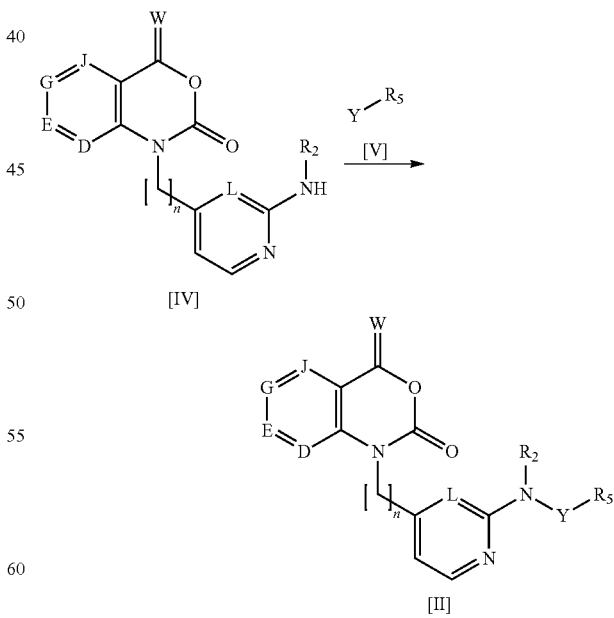

Scheme 2: General method for the preparation of compounds of general formula (II).

Nitrogen substituted anhydrides of general formula [IV] can be prepared from anhydrides of general formula [VI] as depicted in Scheme 3. Treatment of anhydrides of general formula [VI] with alcohols [VII], where LG=OH in a Mitsunobu-like reaction, such as with triphenylphosphine and diethyl azodicarboxylate (DEAD) or diisopropyl azodicarboxylate in a suitable solvent not limited to but such as tetrahydrofuran or diethylether. Alternatively N-alkylated anhydrides of general formula [IV] can be prepared by treatment of [VI] with a suitable base such as sodium carbonate or sodium hydride followed by alkylation with an appropriate alkyl halide [VII] where LG=Cl, Br, I. Non-limiting examples of such preparations have been described by e.g. G. M. Coppola: *Synthetic Communications* (2002), 32, 1009-1013 and references herein and in WO 00/27819.

The anhydrides of general formula [VI] are either commercially available or can be readily prepared using procedures well-known to a person skilled in the art. Non-limiting examples of such preparations have been described by G. M. Coppola: *Synthesis* (1980), 505-536; S. Jonsson et. al.: *J. Med. Chem.* (2004), 47, 2075-2088; J. Clews et al.: *Tetrahedron* (2000), 56, 8735-8746 and U.S. Pat. No. 3,887,550.

Scheme 3: General method for the preparation of Nitrogen substituted anhydrides of general formula [IV] from anhydrides of general formula [VI].

The starting materials [III] and [VIII] are commercially available or can by synthesised by standard methods familiar to those skilled in organic synthesis.

Whilst Schemes 1, 2 and 3 above show one possible synthesis route, it will be appreciated that other synthesis routes are also possible. For example the order of the steps shown in Schemes 1 and 2 could be swapped such that the acylation or thioacylation would be the final step with the amide or thioamide formation immediately preceding that.

GENERAL PROCEDURES, PREPARATIONS AND EXAMPLES $^1$H nuclear magnetic resonance (NMR) spectra were usually recorded at 300 MHz and $^{13}$C NMR spectra at 75.6 MHz. Chemical shift values ($\delta$, in ppm) are quoted in the specified solvent relative to internal tetramethylsilane ($\delta$=0.00) or chloroform ($\delta$=7.25) or deuteriochloroform ($\delta$=76.81 for $^{13}$C NMR) standards. The value of a multiplet, either defined (doublet (d), triplet (t), quartet (q)) or not (m) at the approximate mid point is given unless a range is quoted. (bs) indicates a broad singlet. The organic solvents used were usually anhydrous. Chromatography was performed on Merck silica gel 60 (0.040-0-063 mm). The solvent ratios indicated refer to v:v unless otherwise noted.

The following abbreviations have been used throughout:
ATP Adenosine triphosphate
BSA Bovine Serum Albumin
DCM dichloromethane
DMF N,N'-Dimethylformamide
DMSO dimethyl sulfoxide
Et ethyl
Eq equivalent(s)
h hour(s)
L liter
LG Leaving group
m milli
M Molar (mol/l)
Me methyl
MHz Mega Hertz
NMR nuclear magnetic resonance
o/n Overnight
rt room temperature
SEB Supplement enzymatic buffer
RT Retention time
TBS Tris-buffered saline
THF tetrahydrofuran
Tris Tris(hydroxymethyl)aminomethane
v volume

TABLE 1

Compounds of general formula [I] (W = oxygen; $R_1$, $R_2$ and $R_3$ = hydrogen, n = 1

| Compound | Example | D | E | G | J | L | $R_4$ | Y | $R_5$ |
|---|---|---|---|---|---|---|---|---|---|
| 101 | 1 | CH | CH | CH | CH | CH | | —C(O)— | |

TABLE 1-continued

Compounds of general formula [I] (W = oxygen; $R_1$, $R_2$ and $R_3$ = hydrogen, n = 1)

[I]

| Compound | Example | D | E | G | J | L | R₄ | Y | R₅ |
|----------|---------|---|---|---|---|---|-----|-----|-----|
| 102 | 2 | CH | CH | CH | CH | CH | cyclopentylmethyl | —C(O)— | tert-butyl (CH₃) |
| 103 | 3 | CH | CH | CH | CH | CH | 2-ethylbutyl | —C(O)— | tert-butyl (CH₃) |
| 104 | 4 | CH | CH | CH | CH | CH | 2-ethylbutyl | —C(O)— | oxazol-5-yl |
| 105 | 5 | CH | CH | CH | CH | CH | cyclopentylmethyl | —C(O)— | furan-2-yl |
| 106 | 6 | CH | CH | CH | CH | CH | isopentyl | —C(O)— | furan-2-yl |
| 107 | 7 | CH | CH | CH | CH | CH | neopentyl-methyl | —C(O)— | furan-2-yl |
| 108 | 8 | CH | CH | CH | CH | CH | cyclohexenylmethyl | —C(O)— | furan-2-yl |
| 109 | 9 | CH | CH | CH | CH | CH | 2-ethylbutyl | —C(O)— | furan-2-yl |

General Procedure for Preparation of Compounds with Formula X, wherein R5 is as Stated Above:

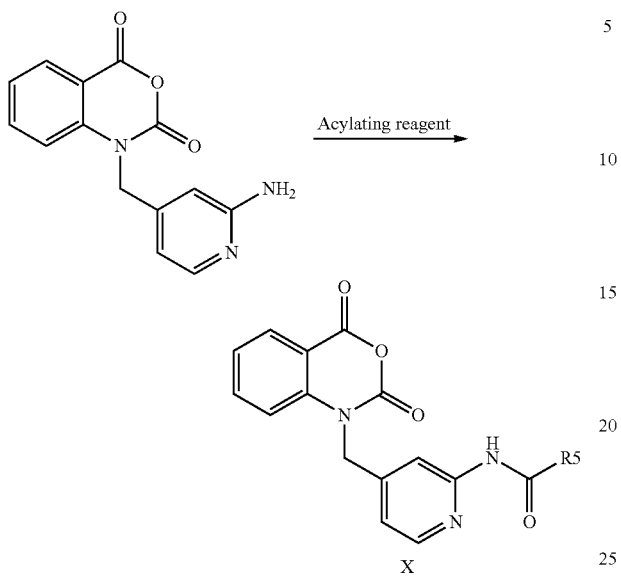

1-(2-Amino-pyridin-4-ylmethyl)-1H-benzo[d][1,3]oxazine-2,4-dione (5 mmol) (prepared according to the procedure in WO2005054179) was dissolved in dry pyridine (20 mL). The acylating reagent (15 mmol, 3 eq) was added drop-wise during 10 minutes. The reaction was left overnight at rt. The solvent was removed in vacuo. The crude was redissolved in EtOAc (100 mL) and washed with water (3×30 mL) and NaCl (sat, 30 mL), then dried over $Na_2SO_4$ and evaporated in vacuo. The compounds were used without further purification.

Preparation 1 (Compound 501)

N-[4-(2,4-Dioxo-4H-benzo[d][1,3]oxazin-1-ylmethyl)-pyridin-2-yl]-acetamide

Acylating reagent: Acetyl chloride
Compound 501 was obtained as white crystals and used without further purification.
$^1H$ NMR (DMSO-$d_5$) δ=10.49 (1H, s), 8.22 (1H, d), 8.07 (2H, m), 7.75 (1H, m), 7.33 (1H, t), 7.20 (1H, d), 7.09 (1H, m), 5.32 (2H, s), 2.07 (3H, s).

Preparation 2 (Compound 502)

[4-(2,4-Dioxo-4H-benzo[d][1,3]oxazin-1-ylmethyl)-pyridin-2-yl]-carbamic acid methyl ester Acylating reagent: Methyl chloroformate
Compound 502 was obtained as a 57:43 mixture of starting material and compound 502 respectively. The mixture was used without further purification.

Preparation 3 (Compound 503)

Oxazole-5-carboxylic acid [4-(2,4-dioxo-4H-benzo[d][1,3]oxazin-1-ylmethyl)-pyridin-2-yl]-amide Acylating reagent: Oxazole-5-carbonoyl chloride, generated from oxazole-5-carboxylic acid by standard treatment with 1.5 eq oxalyl chloride in DCM and catalytic amounts of DMF Compound 503 was obtained as a 70:30 mixture of starting material, impurities and compound 503 respectively. The mixture was used without further purification.

Preparation 4 (Compound 504)

Furan-2-carboxylic acid [4-(2,4-dioxo-4H-benzo[d][1,3]oxazin-1-ylmethyl)-pyridin-2-yl]-amide Acylating reagent: Furan-2-carbonoyl chloride
Compound 504 was obtained as a 71:29 mixture of starting material and compound 504 respectively. The mixture was used without further purification.

Preparation 5 (Compound 505)

3-Ethylpentanenitrile

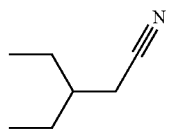

A mixture of 3-chloromethylpentane (25 g, 207 mmol) and NaCN (15 g, 306.1 mmol) in DMSO (150 mL) was stirred at 100° C. for 18 h. The mixture was extracted twice with $Et_2O$. The combined organic phases were washed with brine, dried over $MgSO_4$, and concentrated in vacuo, giving the title compound (23 g) as a yellowish liquid.
$^1H$ NMR (DMSO-$d_6$): δ (ppm)=2.48 (2H, d), 1.58-1.23 (5H, m), 0.87 (6H, d).

Preparation 6 (Compound 506)

3-Ethylpentylamine hydrochloride

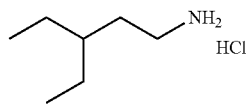

To a solution of 3-ethylpentanenitrile (23 g, 207 mmol) was added Na (15 g, 652.2 mmol) over one hour period. The mixture was heated reflux for 1 h. The reaction solution was then poured into $H_2O$ and extracted twice with $CH_2Cl_2$. The combined organic phases were dried over $MgSO_4$, concentrated to the half of the original volume, acidified with 4 N HCl in 1,4-dioxane. The solution was concentrated to dryness. The residue was purified by crystallization from $CH_3CN$, giving the title compound (10 g) as a white solid.
$^1H$ NMR (DMSO-$d_6$): δ (ppm)=8.20-8.00 (3H, bs), 2.80-2.65 (2H, m), 1.60-1.50 (2H, m), 1.32-1.19 (5H, m), 0.83 (6H, t).

General Procedure for Preparation of Compounds with Formula Z:

An isatoic acid derivative (0.07 mmol, without correcting for any impurities and obtained as described in preparation 1 to 4) was dissolved in dry DMF (0.2 mL). An amine (0.077 mmol) dissolved in pyridine (0.2 mL) was added and the reaction mixture was agitated o/n at rt. The reaction mixture was filtered and concentrated in vacuo. The crude was redissolved in DMF (0.5 mL) and purified by preparative HPLC/MS.

Using this procedure the following compounds of the present invention were obtained:

Example 1

Compound 101

(4-{[2-(3,3-Dimethyl-butylcarbamoyl)-phenylamino]-methyl}-pyridin-2-yl)-carbamic acid methyl ester Amine: 3,3-Dimethylbutylamine
Isatoic acid derivative: Compound 502 from example 2
LC/MS: (m/z) 385.2 (MH+); RT=6.21 min; purity (UV)=100%.
$^1$H NMR (DMSO-$d_6$) δ=10.11 (1H, s), 8.33 (2H, m), 8.16 (1H, d), 7.82 (1H, d), 7.53 (1H, d), 7.16 (1H, m), 6.98 (1H, m), 6.56 (1H, t), 6.47 (1H, d), 4.41 (2H, d), 3.64 (3H, s), 0.93 (9H, s).

Example 2

Compound 102

2-[(2-Acetylamino-pyridin-4-ylmethyl)-amino]-N-(2-cyclopentyl-ethyl)-benzamide

Amine: 2-Cyclopentylethylamine
Isatoic acid derivative: Compound 501 from example 1
LC/MS: (m/z) 381.2 (MH+); RT=5.74 min; purity (UV)=100%
$^1$H NMR (DMSO-$d_6$) δ=10.43 (1H, s), 8.20 (1H, d), 8.07 (1H, s), 7.54 (1H, d), 7.17 (1H, t), 7.01 (1H, d), 6.56 (1H, t), 6.48 (1H, d), 4.40 (2H, d), 3.24 (2H, m), 2.06 (3H, s), 1.78 (3H, m), 1.55 (6H, m), 1.10 (2H, m).

Example 3

Compound 103

2-[(2-Acetylamino-pyridin-4-ylmethyl)-amino]-N-(3-ethyl-pentyl)-benzamide

Amine: 3-Ethylpentylamine hydrochloride obtained in preparation 6
Isatoic acid derivative: Compound 501 from example 1
$^1$H NMR (DMSO-$d_6$) δ=10.43 (1H, s), 8.32 (2H, m), 8.20 (1H, d), 8.05 (1H, s), 7.52 (1H, d), 7.17 (1H, t), 7.01 (1H, d), 6.56 (1H, t), 6.48 (1H, d), 4.41 (2H, d), 3.23 (2H, m), 1.49 (2H, m), 1.31 (5H, m), 0.85 (6H, d).

Example 4

Compound 104

Oxazole-5-carboxylic acid (4-{[2-(3-ethyl-pentylcarbamoyl)-phenylamino]-methyl}-pyridin-2-yl)-amide Amine: 3-Ethylpentylamine hydrochloride obtained in preparation 6
Isatoic acid derivative: Compound 503 obtained in preparation 3
$^1$H NMR (DMSO-$d_5$) δ=10.95 (1H, s), 8.63 (1H, s), 8.32 (3H, m), 8.20 (1H, s), 8.11 (1H, s), 7.54 (1H, d), 7.18 (1H, t), 7.12 (1H, d), 6.57 (1H, t), 6.50 (1H, d), 4.48 (2H, d), 3.24 (2H, m), 1.49 (2H, m), 1.29 (5H, m), 0.84 (6H, d).

Example 5

Compound 105

Furan-2-carboxylic acid (4-{[2-(2-cyclopentyl-ethylcarbamoyl)-phenylamino]-methyl}-pyridin-2-yl)-amide Amine: 2-Cyclopentylethylamine
Isatoic acid derivative: Compound 504 obtained in preparation 4
LC/MS: (m/z) 433.2 (MH+); RT=6.64 min; purity (UV)=100%

Example 6

Compound 106

Furan-2-carboxylic acid (4-{[2-(4-methyl-pentylcarbamoyl)-phenylamino]-methyl}-pyridin-2-yl)-amide Amine: 4-Methylpentylamine
Isatoic acid derivative: Compound 504 obtained in preparation 4
LC/MS: (m/z) 421.2 (MH+); RT=6.51 min; purity (UV)=100%

Example 7

Compound 107

Furan-2-carboxylic acid (4-{[2-(3,3-dimethyl-butyl-carbamoyl)-phenylamino]-methyl}-pyridin-2-yl)-amide Amine: 3,3-Dimethylbutylamine
Isatoic acid derivative: Compound 504 obtained in preparation 4
LC/MS: (m/z) 421.1 (MH+); RT=6.44 min; purity (UV)=100%

Example 8

Compound 108

Furan-2-carboxylic acid (4-{[2-(2-cyclohex-1-enyl-ethylcarbamoyl)-phenylamino]-methyl}-pyridin-2-yl)-amide Amine: 2-Cyclohex-1-enyl-ethylamine
Isatoic acid derivative: Compound 504 obtained in preparation 4
LC/MS: (m/z) 445.1 (MH+); RT=6.67 min; purity (UV)=98%

Example 9

Compound 109

Furan-2-carboxylic acid (4-{[2-(3-ethyl-pentylcarbamoyl)-phenylamino]-methyl}-pyridin-2-yl)-amide Amine: 3-Ethylpentylamine hydrochloride obtained in preparation 6
Isatoic acid derivative: Compound 504 obtained in preparation 4
LC/MS: (m/z) 435.1 (MH+); RT=6.81 min; purity (UV)=100%

Example 10

KDR Assay—HTRF KinEASE-TK

The compounds to be tested were dissolved in DMSO at 10 mM, stored at −20° C. and protected from light. The maximum concentration of DMSO in the in vitro assay was 0.75%. Control samples received the same concentration of solvent as the samples treated with the test compounds.

For the kinase assays, the HTRF KinEase™-TK kit (CisBio (#62TKOPEJ) was used. All components in HTRF KinEase™-TK kit were handled according to suppliers description. Briefly, DMSO stock solution of compounds (100% DMSO) were prediluted to 6% DMSO in 50 mM Hepes-buffer+0.05% BSA (Sigma Aldrich (A3294)) before transferring 1 µl to a 384-well Proxyplate (Perkin Elmer (#6008289) at RT. Kinase Substrate (2 µL, CisBio) was added to Proxyplate with compound. Enzyme mix (5 µL, Millipore (14-630)) with ATP (100 µM, Sigma Aldrich (A7699)), MgCl$_2$ (5 mM; Sigma Aldrich M1028) and SEB (50 nM, CisBio) was added to start the reaction. The plates were incubated for 15 minutes at rt. The assay was stopped by addition of Detection mix (4 µL, CisBio) and plates were sealed and spun for 1 min at 1000 rpm. The plates were incubated in darkness overnight at rt. The plates were read on an Envision (Perkin Elmer) plate reader. Signal from two wave lengths (665 and 620 nm) upon excitation at 340 nm in accordance to manufactures instructions. Briefly, fluorescence was measured for 400 µs between flashes after a delay time of 400 µs. The background measured in the absence of enzyme was subtracted from all samples. The molar concentrations that inhibited 50% of the maximal enzymatic activity (IC$_{50}$) were calculated using a four-parameter sigmoid curve fit model of the dose-response curve, based on the following equation: $y=((a-d)/(1+(x/c)^b))+d$; where a is the minimum value, d is the maximum value, c is the IC50 value and d is the slope factor.

The in vitro KDR inhibitory activities of compounds of general formula (I) of the present invention are listed in Table 2.

TABLE 2

| In vitro KDR inhibition | | |
|---|---|---|
| Compound | Example | VEGFR-2 IC$_{50}$ (nM) |
| 101 | 1 | 11 |
| 102 | 2 | 8 |
| 103 | 3 | 19 |
| 104 | 4 | 15 |
| 105 | 5 | 43 |
| 106 | 6 | 17 |
| 107 | 7 | 39 |
| 108 | 8 | 44 |
| 109 | 9 | 53 |

Example 11

Metabolic Stability

The metabolic stability is tested in human liver microsomes (In Vitro Technologies, pooled mixed sexes, 20 mg/mL); a subcellular fraction containing major drug-metabolizing phase I enzymes, including the cytochrome P450 (CYP) family and flavin monooxygenases (FMO). The apparent clearance (mL/min/kg) is calculated as a measurement of test compound elimination from the liver.

Procedure: A human microsome incubation mixture (0.5 mg microsomal protein/mL) in phosphate buffer (pH 7.4, 100 mM KH$_2$PO$_4$/10 mM MgCl$_2$) is mixed with NADPH (1 mM). The mixture is pre-heated (7 min) to 37° C., test compound (0.5 µM) is added, and the mixture is incubated for 30 minutes. Incubations are run in duplicate and performed by a Tecan RSP. Samples are withdrawn at 0, 5, 10, 20, and 30 min and mixed with methanol containing internal standard to terminate all enzyme activity and precipitate proteins. A negative control without NADPH (to detect nonspecific protein binding or heat instability) and a negative control without microsomes (for assessing compound stability in the absence of active enzymes) are performed. Samples are analysed by LC-MS/MS.

Data analysis: The logarithm of the peak area ratios of test compound to internal standard versus incubation time is plotted in a graph. The rate constant (k) of test compound depletion is calculated from the linear part of the curve (Eq. 1) and the half-time (t$_{1/2}$) is calculated from the slope (Eq. 2).

$$\text{Rate constant}(k)(\text{min}^{-1})=-\text{slope} \qquad \text{Eq. 1}$$

$$\text{Half-time}(t_{1/2})(\text{min})=\ln 2/k \qquad \text{Eq. 2}$$

Intrinsic clearance (Cl$_{int}$) is calculated from the rate constant (k) (min$^{-1}$) and the protein concentration (0.5 mg/mL) (Eq. 3).

$$\text{Cl}_{int}(\text{mL/min/mg protein})=k/\text{Protein concentration} \qquad \text{Eq. 3}$$

Conversion to apparent clearance ($Cl_{app}$) is performed by multiplying $Cl_{int}$ with the amount of microsomal protein per g liver (45 mg/g) and the liver weight per kg body (20 g/kg) (Eq. 4)

$Cl_{app}$(mL/min/kg)=$Cl_{int}$×(mg microsomal protein/g liver)×(g liver/kg body weight)     Eq. 4

Interpretation: Apparent intrinsic clearance below approximately 10 mL/min/kg (corresponding to extraction ratio of approx. 30%) is considered as low clearance (high metabolic stability). Apparent intrinsic clearance above approximately 60 mL/min/kg (corresponding to extraction ratio of approx. 75%) is considered as high clearance (low metabolic stability). The following HLM assay reference compounds give the following intrinsic clearance values:
Warfarin (Sigma-Aldrich A 2250)=<10 mL/min/kg (low clearance)
Propranolol hydrochloride (Sigma-Aldrich P0884)=25-35 mL/min/kg (medium clearance)
Midazolam (Ultrafine Chemicals UC-429)=>200 mL/min/kg (high clearance)

The metabolic stability of compounds of general formula [I] of the present invention are listed in Table 3.

TABLE 3

Metabolic stability:

| Compound | Example | [1]HLM (mL/min/kg) |
|---|---|---|
| 101 | 1 | 135 |
| 102 | 2 | >200 |
| 103 | 3 | >200 |
| 104 | 4 | 120 |
| 105 | 5 | >200 |
| 106 | 6 | >200 |
| 107 | 7 | >200 |
| 108 | 8 | >200 |
| 109 | 9 | >200 |

The invention claimed is:
1. A compound of general formula I

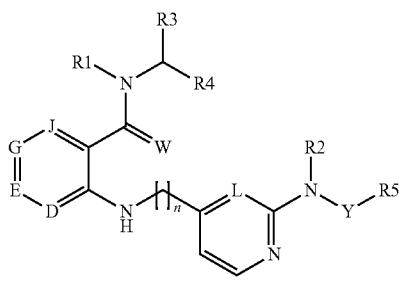

[I]

wherein $R_1$ represents hydrogen or a straight, saturated or unsaturated $C_{1-2}$ hydrocarbon radical;
$R_2$ and $R_3$ represent hydrogen or a straight or branched saturated or unsaturated $C_{1-6}$ hydrocarbon radical;
D, E, G, J, and L all represent —CH—;
n represents an integer from 1-2;
W represents oxygen or sulphur;
$R_4$ represents $C_{1-6}$alkyl, $C_{2-6}$alkenyl, $C_{3-6}$cycloalkyl, $C_{3-6}$cycloalkenyl, $C_{2-5}$heterocycloalkyl, $C_{2-5}$heterocycloalkenyl, wherein said $C_{1-6}$alkyl, $C_{2-6}$alkenyl, $C_{3-6}$cycloalkyl, $C_{3-6}$cycloalkenyl, $C_{2-5}$heterocycloalkyl, $C_{2-5}$heterocycloalkenyl, are optionally substituted by one or more, same or different substituents independently selected from the group consisting of hydrogen, $C_{1-4}$alkyl, $C_{2-4}$alkenyl, $C_{3-6}$cycloalkyl, and $C_{3-6}$cycloalkenyl, wherein said $C_{1-4}$-alkyl, $C_{1-4}$alkenyl, $C_{3-6}$cycloalkyl and $C_{3-6}$cycloalkenyl are optionally substituted by one or more, same or different substituents independently selected from methyl and ethyl;
or $R_3$ and $R_4$ together form part of a $C_{3-8}$cycloalkyl;
Y represents carbonyl or thioxo;
$R_5$ represents hydrogen, $C_{1-6}$alkyl, $C_{1-6}$alkoxy, $C_{3-8}$cycloalkyl, $C_{3-8}$cycloalkenyl, $C_{2-7}$heterocycloalkyl or $C_{2-7}$heteroaryl, wherein said $C_{1-6}$alkyl, $C_{1-6}$alkoxy, $C_{3-8}$cycloalkyl, $C_{2-7}$heterocycloalkyl or $C_{2-7}$heteroaryl are optionally substituted with one or more substituents independently selected from the group consisting of cyano, $C_{1-6}$alkyl, $C_{1-6}$alkoxycarbonyl or $C_{1-6}$alkylcarbonyloxy;
and pharmaceutically acceptable salts thereof.

2. A compound according to claim 1 wherein W represents oxygen.

3. A compound according to any one of claims 1-2 wherein Y is C(O).

4. A compound according to claim 1 wherein $R_1$, $R_2$ and $R_3$ represent hydrogen.

5. A compound according to claim 1 wherein n is 1.

6. A compound according to claim 1 wherein W is oxygen, Y is —C(O)—, $R_1$, $R_2$ and $R_3$ represent hydrogen, and n is 1.

7. A compound according to claim 1 wherein R5 represents hydrogen, methyl, ethyl, propyl, methoxy, ethoxy, $C_{3-6}$cycloalkyl, $C_{4-6}$cycloalkenyl, $C_{2-5}$heterocycloalkyl or $C_{2-5}$heteroaryl, wherein said methyl, ethyl, propyl, methoxy, ethoxy, $C_{3-6}$cycloalkyl, $C_{4-6}$cycloalkenyl, $C_{2-5}$heterocycloalkyl or $C_{2-5}$heteroaryl are optionally substituted with one or more substituents independently selected from the group consisting of cyano, methyl, ethyl, propyl, methoxycarbonyl, ethoxycarbonyl, propoxycarbonyl, methylcarbonyloxy, or ethylcarbonyloxy.

8. A compound according to claim 1 wherein $R_5$ represents hydrogen, methyl, methoxy, ethoxy, cyanomethyl, cyclopropyl, methoxycarbonylethyl, methylcarbonyloxymethyl, tetrahydrofuranyl, furyl, thienyl, isoxazolyl, oxazolyl, thiazolyl, oxadiazolyl, thiadiazolyl or triazolyl, all of which are optionally substituted with methyl.

9. A compound according to claim 1 wherein $R_3$ and $R_4$ forms part of a cyclopropyl, cyclobutyl, cyclopentyl or cyclohexyl ring.

10. A compound according to claim 1 selected from the group consisting of
(4-{[2-(3,3-Dimethyl-butylcarbamoyl)-phenylamino]-methyl}-pyridin-2-yl)-carbamic acid methyl ester (compound 101);
2-[(2-Acetylamino-pyridin-4-ylmethyl)-amino]-N-(2-cyclopentyl-ethyl)-benzamide (compound 102);
2-[(2-Acetylamino-pyridin-4-ylmethyl)-amino]-N-(3-ethyl-pentyl)-benzamide (compound 103);
Oxazole-5-carboxylic acid (4-{[2-(3-ethyl-pentylcarbamoyl)-phenylamino]-methyl}-pyridin-2-yl)-amide (compound 104);
Furan-2-carboxylic acid (4-{[2-(2-cyclopentyl-ethylcarbamoyl)-phenylamino]-methyl}-pyridin-2-yl)-amide (compound 105);
Furan-2-carboxylic acid (4-{[2-(4-methyl-pentylcarbamoyl)-phenylamino]-methyl}-pyridin-2-yl)-amide (compound 106);
Furan-2-carboxylic acid (4-{[2-(3,3-dimethyl-butylcarbamoyl)-phenylamino]-methyl}-pyridin-2-yl)-amide (compound 107);

Furan-2-carboxylic acid (4-{[2-(2-cyclohex-1-enyl-ethyl-carbamoyl)-phenylamino]-methyl}-pyridin-2-yl)-amide (compound 108);

Furan-2-carboxylic acid (4-{[2-(3-ethyl-pentylcarbamoyl)-phenylamino]-methyl}-pyridin-2-yl)-amide (compound 109).

11. A pharmaceutical composition comprising a compound according to claim 1 or a pharmaceutically acceptable salt thereof together with a pharmaceutically acceptable vehicle or excipient.

* * * * *